United States Patent [19]

Göhring et al.

[11] Patent Number: 5,352,344
[45] Date of Patent: Oct. 4, 1994

[54] METHOD AND APPARATUS FOR MEASURING THE OXYGEN POTENTIAL OF A HEAT-TREATMENT FURNANCE

[75] Inventors: Werner Göhring, Kleve; Maz Roggatz, Goch-Nierswalde; Bernd Edenhofer, Kleve, all of Fed. Rep. of Germany

[73] Assignee: Ipsen Industries International Gesellschaft mit beschränkter Haftung, Kleve, Fed. Rep. of Germany

[21] Appl. No.: 988,343

[22] Filed: Dec. 8, 1992

Related U.S. Application Data

[63] Continuation-in-part of Ser. No. 664,416, Feb. 28, 1991, abandoned, which is a continuation-in-part of Ser. No. 418,020, Oct. 6, 1989, abandoned.

[30] Foreign Application Priority Data

Oct. 6, 1988 [DE] Fed. Rep. of Germany ....... 3833968

[51] Int. Cl.[5] ............................................. G01N 27/417
[52] U.S. Cl. ................................ 204/153.18; 204/421; 204/427; 204/428
[58] Field of Search ..................... 204/153.18, 421-429

[56] References Cited

U.S. PATENT DOCUMENTS

| | | | |
|---|---|---|---|
| 3,454,486 | 7/1969 | Davies | 204/427 |
| 3,468,780 | 9/1969 | Fischer | 204/422 |
| 3,481,855 | 12/1969 | Kolodney et al. | 204/15 |
| 3,546,086 | 12/1970 | Sayles | 204/427 |
| 3,657,094 | 4/1972 | Hans et al. | 204/422 |
| 3,776,831 | 12/1973 | Roy et al. | 204/422 |
| 3,791,937 | 2/1974 | Besson et al. | 204/427 |
| 3,883,408 | 5/1975 | Kim et al. | 204/424 |
| 4,049,524 | 9/1977 | Togawa et al. | 204/427 |
| 4,193,857 | 3/1980 | Bannister et al. | 204/426 |
| 4,257,863 | 3/1981 | Hoffman | 204/427 |
| 4,388,155 | 6/1983 | Chamberland et al. | 204/426 |
| 4,427,525 | 1/1984 | Lin et al. | 204/427 |

*Primary Examiner*—T. Tung
*Attorney, Agent, or Firm*—Robert W. Becker & Associates

[57] ABSTRACT

A probe for measuring oxygen potential, especially to determine the carbon-transfer properties of a furnace atmosphere containing the gases $H_2$, CO, and $CH_4$, with the probe having an oxygen ion conducting, solid measuring electrolyte with a contact electrode in the furnace atmosphere and a contact electrode in a reference medium that has a known oxygen concentration. To improve the accuracy of the measurement, an oxygen ion conductive compensation electrolyte in the form of a detachable solid body is connected between the contact electrode in the furnace atmosphere and the solid measuring electrolyte.

15 Claims, 1 Drawing Sheet

METHOD AND APPARATUS FOR MEASURING THE OXYGEN POTENTIAL OF A HEAT-TREATMENT FURNANCE

This application is a continuation-in-part, of application Ser. No. 664,416 filed Feb. 28, 1991 now abandoned which in turn is a continuation-in-part application of Ser. No. 418,020 filed Oct. 6, 1989 now abandoned.

BACKGROUND OF THE INVENTION

The present invention relates to a method and a probe for measuring the oxygen potential of a furnace atmosphere, especially to determine the carbon-transfer properties of a furnace atmosphere containing the gases $H_2$, CO, and $CH_4$, with the probe having an oxygen ion conducting, solid measuring-electrolyte with a contact electrode in the furnace atmosphere, and having a contact electrode in a reference medium that has a known oxygen potential.

A probe of this general type is known, and comprises an oxygen ion conducting, solid electrolyte, especially zirconium oxide, one wall of which is in contact with the furnace atmosphere, and the other wall of which is in contact with the reference medium of known oxygen potential, generally air. Varying concentrations of oxygen atoms, oxygen ions, and electrons form on the two wall surfaces in conformity with the different oxygen concentrations of the furnace atmosphere on the one hand and the reference medium on the other hand. These different concentrations can be measured as an electrical voltage that thus represents the difference between the two oxygen concentrations. The voltage is picked up by electron-conductive contact electrodes that are in contact with the respective wall of the solid electrolyte.

The function of measuring electrodes for determining the oxygen potential between two media or atmospheres separated by an oxygen-conducting electrolyte is based on the Nernst Law. According to the Nernst Law, the electric potential measured between the two atmospheres depends only on the partial pressure differential of oxygen in the two atmospheres:

$$E(mV) = \frac{RT}{4F} \cdot \ln \frac{p(O_2)}{p'(O_2)} = 0.0496 \, T \ln \frac{p(O_2)}{p'(O_2)}$$

As can be seen from the equation, no other factor than the partial pressure differential determines the measured voltage. The thickness of the electrolyte has no influence on the electric potential resulting from the partial pressure differential between the two atmospheres. Accordingly, making the electrolyte thicker or applying a further sintered layer (i.e., a layer that due to the sintering process fuses with the electrolyte and becomes a unitary part with it) of the same electrolyte material onto the original electrolyte does not affect the measured values.

Oxygen probes of the aforementioned type are frequently used to regulate the carbon level (C-level) of carburizing atmospheres in heat-treatment furnaces. Such carburization atmospheres are principally comprised of the gases carbon monoxide (CO), hydrogen ($H_2$), and nitrogen ($N_2$), with greater or lesser fractions of hydrocarbons, predominantly $CH_4$. The greater the $CH_4$ fraction in the furnace atmosphere, the simpler and more economical is the production thereof, and the greater is the carbon-transfer rate that can be achieved out of the furnace atmosphere onto the surface of the workpiece. For the regulation of the carburization, the C-level of the furnace atmosphere can be calculated from the measured value of the oxygen probe that is in communication with the furnace atmosphere, the CO content of the furnace atmosphere, and the temperature of the furnace chamber. Critical to the satisfactory functioning of the oxygen probe in the context described is that the contact electrode that is in communication with the furnace atmosphere be embodied, at least at the contact location to the solid electrolyte, of an electrically conductive element that does not catalytically cause a $CH_4$ decomposition. Known examples of such materials that do not cause the catalytic decomposition of $CH_4$ are the metals copper, silver, gold, or palladium. However, even with the use of the aforementioned materials as contact electrodes in the furnace atmosphere, the drawback is that a drifting of the measured value that is obtained to a constantly higher indication can occur, resulting in the danger of errors in the regulation of the carbon level of the furnace atmosphere.

The contact surfaces between the solid electrolyte on the one hand and the contact electrode furnace atmosphere or reference atmosphere on the other hand, and at which surfaces the various oxygen potentials are read off, are critical for the measurement result due to an electrode reaction that occurs even if the contact electrodes are made of a material that does not catalytically cause decomposition of $CH_4$.

As previously described, the oxygen potential that is to be measured is characterized by the concentrations of oxygen atoms, oxygen ions, and electrons at the measuring location. A prerequisite for a precise measurement is therefore that the measuring process does not disturb the equilibrium concentrations between the measuring location and the surrounding atmosphere. Such a disruption occurs if due to a strong reaction of the oxygen ions that emerge from the electrolyte with the furnace atmosphere, i.e., $CH_4$ (electrode reaction), more oxygen ions are removed from the solid electrolyte than can be incorporated into the electrolyte at the reference air side. As a consequence, at the furnace electrode the oxygen potential then becomes lower than in the surrounding furnace atmosphere. Thus, with regard to the measurement result, the measured oxygen potential is too low and deviates from the real value. With the heretofore known oxygen probes, the aforementioned equilibrium between the measuring location on the furnace electrode and the surrounding furnace atmosphere can be maintained to only a certain strength of the electrode reaction. The higher the furnace temperature and the more the C-level increases, the greater is the electrode reaction and the more imprecise is the measurement.

The cause of the aforementioned drifting of the measured value is that during the course of time, due to an increasingly better contact between electrode and electrolyte, the electrode reaction disadvantageously becomes continuously greater.

It is an object of the present invention to improve the oxygen probe of the aforementioned general type in such a way that errors in measurement, especially a drifting of the measured value to increased probe voltage, are avoided or at least reduced, and hence to provide an oxygen probe that is characterized by an improved measurement precision and provides a measured value that represents the driving force of the material transfer from the furnace atmosphere to the surface of the workpieces. In addition, the aforementioned drawbacks are to be avoided.

It is a particular object of the present invention to develop a probe with which the oxygen potential of the atmosphere produced in the furnace chamber of a heat-treatment furnace can be measured in an error-free manner at a high carburization rate even during an extended operation.

BRIEF DESCRIPTION OF THE DRAWING

These and other objects and advantages of the present invention will appear more clearly from the following specification in conjunction with the accompanying schematic drawing, in which.

SUMMARY OF THE INVENTION

Figure 3:
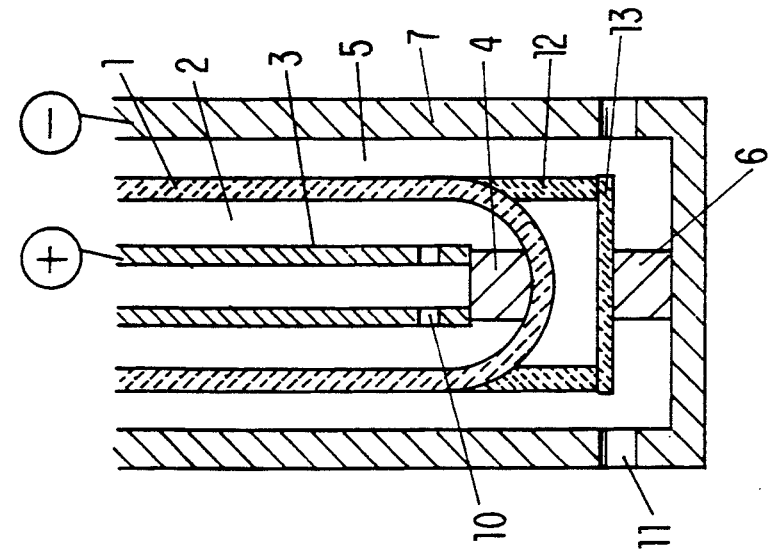
FIG. 3 is a cross-sectional view of a third exemplary embodiment of the inventive oxygen probe.

The probe for measuring the oxygen potential of a furnace atmosphere relative to a reference medium of a known oxygen potential according to the present invention is primarily characterized by:

an oxygen ion conducting solid measuring electrolyte exposed with a first surface to the furnace atmosphere and with a second surface to the reference medium;

a first contact electrode connected to a portion of the first surface in the furnace atmosphere;

a second contact electrode connected to a portion of the second surface in the reference medium; and an oxygen ion conducting compensation electrolyte means for compensating oxygen potential deviations of the measuring electrolyte at the first surface in the furnace atmosphere, the compensation electrolyte means comprising a first detachable solid body connected between the first contact electrode and the portion of the first surface in the furnace atmosphere.

In conventional measuring probes, at the contact location of the solid electrolyte and the contact electrode, due to the presence of the contact electrode material, $CH_4$ present in the furnace atmosphere reacts with oxygen of the electrolyte material at the surface of the measuring electrolyte in the so-called electrode reaction. Oxygen is thus removed from the surface of the measuring electrolyte thus lowering the actual oxygen potential between the furnace atmosphere and the reference atmosphere and falsifying the readings of the measuring electrolyte.

The inventive first solid body (first compensation electrolyte) has the function of removing the contact electrode from the surface of the solid electrolyte thus preventing the electrode reaction according to which in the vicinity of the contact electrode $CH_4$ reacts with the solid electrolyte material that leads to an oxygen depletion at the surface of the measuring electrolyte.

The inventive first compensation electrolyte in the form of a solid is detachable, i.e., it has surface contact with the measuring electrolyte, but is not a unitary part with it and does not form a structural unit with the measuring electrolyte. Accordingly, the first compensation electrolyte and the measuring electrolyte have a physical border between them. The continuity of the crystal lattice is thus interrupted. Thus, the oxygen potential between the reference medium and the furnace atmosphere is created between the two surfaces of the measuring electrolyte and does not continue through the compensation electrolyte. However, due to the oxygen-conducting properties of the compensation electrolyte means, the oxygen ions are further conducted through the first compensation electrolyte to the contact electrode for a correct measurement of the oxygen potential.

Furthermore, the first compensation electrolyte means is exposed only to the furnace atmosphere and therefore an oxygen potential between different surfaces of the compensation electrolyte means is not present. The separate and detachable first compensation electrolyte is thus a "neutral" (with respect to an oxygen potential) interposed body between the surface of the measuring electrolyte exposed to the furnace atmosphere and the contact electrode. By spacing the contact electrode from the measuring electrolyte the electrode reaction, i.e., the reaction of $CH_4$ with oxygen at the surface of the measuring electrolyte induced by the contact electrode, is eliminated.

The probe of the present invention is thus characterized primarily in that oxygen ion conductive compensation electrolyte means in the form of a separate detachable solid body is disposed between the contact electrode in the furnace atmosphere and the solid electrolyte, with such electrolyte means being in contact with both the solid measuring electrolyte and the contact electrode in the furnace atmosphere.

The compensation electrolyte means preferably conducts exclusively oxygen ions and has a common contact location solid electrolyte/compensation electrolyte/furnace atmosphere. With the inventive compensation electrolyte means, the up to now conventional contact location of the electron-conductive contact electrode in the furnace atmosphere with the measuring electrolyte is eliminated. In place thereof, oxygen ions from the common contact location measuring electrolyte/furnace atmosphere/compensation electrolyte are conveyed further within the compensation electrolyte to the electron conductive measurement location.

Preferably, the compensation electrolyte means further comprises a second detachable solid body connected between the second contact electrode and the portion of the second surface in the reference medium.

Pursuant to this expedient specific embodiment of the present invention, a further compensation electrolyte in the form of a solid body (second compensation electrolyte) that conducts exclusively oxygen ions is additionally disposed on the reference side of the measuring electrolyte between the electron-conductive contact electrode that is located there and the measuring electrolyte. This second compensation electrolyte has a common contact location measuring electrolyte/compensation electrolyte/reference medium, and in principle operates in the same manner as does the aforementioned first compensation electrolyte in the furnace atmosphere. By means of this second compensation electrolyte, an increased oxygen ion concentration can also be compensated for. This is especially advantageous at furnace atmospheres under operating conditions with a low ion throughput, for example at low furnace temperature or high oxygen potential. In such a case, the ion consumption at the measuring location in the furnace atmosphere can become lower than the ion production at the measuring location on the reference side. The use of a second compensation electrolyte then prevents an erroneous measurement in the form of overvoltage.

The first and second compensation electrolytes can be a cubic or cylindrical body of $ZrO_2$, preferably in the form of a cylindrical portion out of the same tubular material the measuring electrolyte is made of.

The electron conductive contact electrodes in the furnace atmosphere preferably comprise gold or a platinum alloy that contains predominantly gold. Alternatively, the electron conductive contact electrode in the furnace atmosphere could also comprise a semiconductor, such as silicon carbide. A heat-resistant chromium-nickel steel is preferably used as the material for the electron conductive contact electrode in the reference medium.

The method of the present invention for measuring the oxygen potential of a furnace atmosphere relative to a reference medium of a known oxygen potential comprises the steps of:

exposing an oxygen ion conducting solid measuring electrolyte with a first surface to the furnace atmosphere and with a second surface to the reference medium;

connecting a first contact electrode to a portion of the first surface in the furnace atmosphere;

connecting a second contact electrode to a portion of the second surface in the reference medium; and interposing an oxygen ion conducting compensation electrolyte means that comprises a detachable solid body between the first contact electrode and the portion of the first surface for avoiding oxygen potential deviations of the measuring electrolyte at the first surface in the furnace atmosphere by eliminating contact between the first surface of the measuring electrolyte and the first contact electrode.

The inventive method further comprises the step of connecting a second detachable solid body of the compensation electrolyte means between the second contact electrode and the portion of the second surface in the reference medium.

Further specific features of the present invention will be described in detail subsequently.

DESCRIPTION OF PREFERRED EMBODIMENTS

Figure 1:
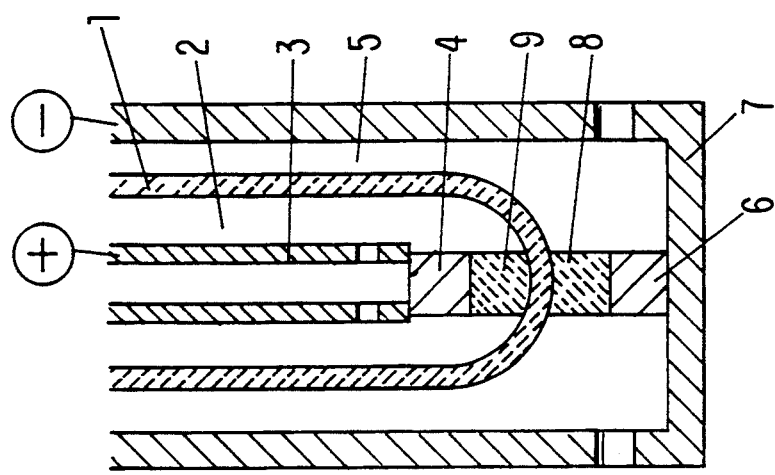
FIG. 1 is a cross-sectional view of one exemplary embodiment of the inventive oxygen probe.

Referring now to the drawing in detail, the oxygen probe illustrated in FIG. 1 comprises a tube 1 that is closed at one end and is a solid electrolyte, in particular of stabilized zirconium oxide, which conducts exclusively oxygen ions. Disposed within the tubular solid electrolyte 1 is a tube 3 made of a heat resistant electron-conductive material via which air 2, as reference medium, is brought into contact with the inner surface of the solid electrolyte 1. The air-supply tube 3 is at the same time embodied as a conductor to pick up or tap the voltage that is produced at the electron-conductive contact electrode 4, also known as an inner electrode. For this purpose, one end of the tube 3 is in contact with the inner electrode 4, with transverse bores 10 being provided to let air pass through to the inner surface of the solid electrolyte 1.

The solid electrolyte 1 is surrounded on the outside by a protective tube 7 that comprises a heat resistant, electron conductive material. The end of the tube 7 is closed and is provided with transverse bores 11 that lead to the furnace atmosphere 5. In this way, the outer surface of the solid electrolyte 1 is constantly in communication with the furnace atmosphere 5. At an electron-conductive contact electrode 6, also known as an outer electrode, the oxygen ions that travel through the solid electrolyte 1 are converted into oxygen atoms and electrons. In the illustrated embodiment, the thereby resulting voltage is conveyed further via the protective tube 7, which is comprised of electron conductive material, to the non-illustrated measuring device, for which purpose the outer electrode 6 on the one hand is connected to the outer surface of the solid electrolyte 1 and on the other hand is connected to the inner surface of the protective tube 7. The measured value is a voltage in millivolts mV that represents the carbon-transfer properties of a furnace atmosphere and can be used to regulate the C-level of carburization atmospheres. Disposed between the outer electrode 6 and the solid or measuring electrolyte 1 is a compensation electrolyte 12 that is a tubular body of the same material as the measuring electrolyte 1. The tubular body 12 is rounded off where it contacts the solid electrolyte 1 in order to assure a good fit. Disposed between the compensation electrolyte 12 and the contact electrode 6 is a precious metal plate 13 that is part of the contact electrode. In other respects, the oxygen probe of the embodiment of FIG. 1 corresponds to the subsequently to be described embodiments of FIGS. 2 and 3, an explanation of which follows.

Figure 2:
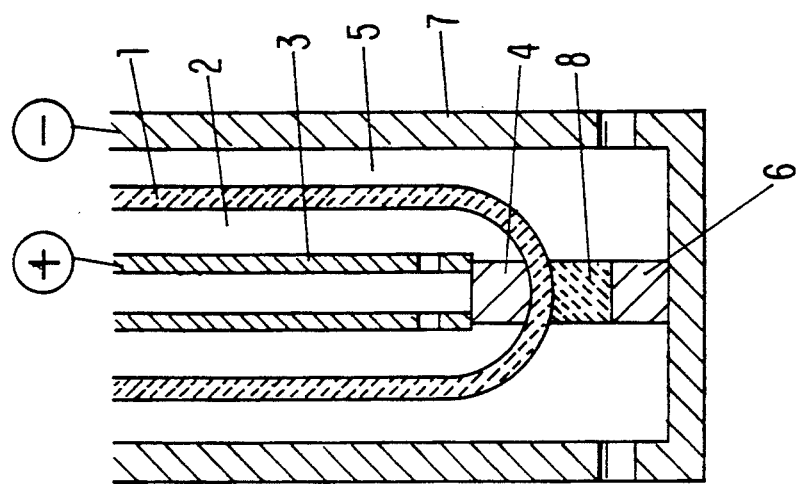
FIG. 2 is a cross-sectional view of a second exemplary embodiment of the inventive oxygen probe.

In the inventive oxygen probe schematically illustrated in FIG. 2, a compensation electrolyte 8 is disposed between the measuring electrolyte 1 and the outer electrode 6. The compensation electrolyte 8 thus communicates with the measuring electrolyte 1, the outer electrode 6, and the furnace atmosphere 5. The compensation electrolyte 8 comprises a material that conducts exclusively oxygen ions, with this material advantageously being zirconium oxide with additives of $Y_2O_3$, CaO, and/or MgO. The electron conductive contact electrode 6 in the furnace atmosphere 5 is made of a material that in a carburization atmosphere can withstand temperatures in a range of from 800° to 1000° C. In the illustrated embodiment, the outer electrode 6 is made of gold or an alloy that predominantly contains gold. However, the precious metals platinum, silver, copper, and alloys thereof could also be successfully used. In the illustrated embodiment, gold was selected as a material because the least amount of chemical absorption of oxygen atoms or molecules is achieved with gold. In addition, gold has a very high chemical resistance, so that an extremely precise measurement can be achieved over a very long service life.

FIG. 3 shows a further embodiment of the inventive oxygen probe, and includes an additional (second) compensation electrolyte 9 that is disposed in the reference medium 2. The second compensation electrolyte 9 is made of the same material as the compensation electrolyte 8 and is disposed between the inner electrode 4 and the measuring electrolyte 1 in such a way that it communicates with the electron conductive contact electrode 4 on the one hand, the inner surface of the measuring electrolyte 1 on the other hand, as well as the reference medium air. For the sake of effectiveness, it is important that the compensation electrolytes be made of material that conducts exclusively oxygen ions.

By the use of the second compensation electrolyte 9 on the reference side with air as the reference medium, austenitic stainless steels and other chromium/nickel steels can advantageously be used as the electron-conductive contact electrode 4 and/or 6 without having to tolerate any drawbacks with regard to measuring precision. As a result, the entire oxygen probe can be produced in a technically more straightforward and economical manner. With the present invention, for the first time the disruptive influence of the electrode reaction between oxygen ions and gases of the furnace atmosphere upon the measuring system of the oxygen probe was recognized and eliminated.

The illustrated oxygen probes can be used to regulate the carbon transfer of fuel/air mixtures introduced into the combustion chamber of heat-treatment furnaces, with the measured value of these probes at a known CO content representing the carbon activity of the furnace atmosphere; this is a value or property that is better suited for regulating the carbon transfer than is the carbon level that is customarily used for this purpose. During the regulation of the carburization atmosphere, the precision of the carbon transfer is improved, particularly at high furnace temperatures. In so doing, it is of particular advantage that the contact electrode does not absorb any carbon, as a result of which the probe can deliver correct measured values close to the carbon black limit. Thus, the carbon transfer can be undertaken at higher carbon activities of the furnace atmosphere than was previously possible, thereby reducing the carburization times. Furthermore, the more rapid indication of the measured value achieved after changes of the furnace atmosphere is advantageous, for example if the diffusion process begins after a carburization process.

The present invention is, of course, in no way restricted to the specific disclosure of the specification and drawing, but also encompasses any modifications within the scope of the appended claims.

What we claim is:

1. A probe for measuring the oxygen potential of a furnace atmosphere relative to a reference medium of a known oxygen potential, especially to determine the carbon-transfer properties of a furnace atmosphere containing the gases $H_2$, CO, and $CH_4$, said probe comprising:

an oxygen ion conducting solid measuring electrolyte exposed with a first surface to said furnace atmosphere and with a second surface to said reference medium;

an oxygen ion conducting compensation electrolyte means for compensating oxygen potential deviations of said measuring electrolyte at said first surface in said furnace atmosphere, said compensation electrolyte means comprising a first solid body detachably connected to a portion of said first surface in said furnace atmosphere;

a first contact electrode connected to said compensation electrolyte means remote from said portion of said first surface; and a second contact electrode connected to a portion of said second surface in said reference medium.

2. A probe according to claim 1, wherein said compensation electrolyte means further comprises a second solid body detachably connected between said second contact electrode and said portion of said second surface in said reference medium.

3. A probe according to claim 1, wherein said compensation electrolyte means is a cubic body of $ZrO_2$.

4. A probe according to claim 1, wherein said compensation electrolyte means is a cylindrical body of $ZrO_2$.

5. A probe according to claim 1, wherein said measuring electrolyte is tubular and wherein said compensation electrolyte means is a cylindrical body made of the same material as said measuring electrolyte, said probe further comprising an intermediate plate of precious metal connected between said compensation electrolyte and said first contact electrode, with said cylindrical body having a first end resting against said portion of said first surface of said measuring electrolyte and a second end connected to said intermediate plate.

6. A probe according to claim 1, wherein said compensation electrolyte means is made of the same material as said measuring electrolyte.

7. A probe according to claim 6, wherein said same material is $ZrO_2$.

8. A probe according to claim 7, wherein said $ZrO_2$ has at least one additive selected from the group consisting of $Y_2O_3$, CaO, and MgO.

9. A probe according to claim 1, wherein said first contact electrode is made of gold.

10. A probe according to claim 1, wherein said first contact electrode is made of an alloy that contains predominantly gold.

11. A probe according to claim 1, wherein said first contact electrode comprises a semiconductor.

12. A probe according to claim 11, wherein said semiconductor is silicon carbide.

13. A probe according to claim 1, wherein said second contact electrode is made of heat-resistant chromium-nickel steel.

14. A method for measuring the oxygen potential of a furnace atmosphere relative to a reference medium of a known oxygen potential, especially to determine the carbon-transfer properties of a furnace atmosphere containing the gases $H_2$, CO, and $CH_4$, said method comprising the steps of:

exposing a first surface of an oxygen ion conducting solid measuring electrolyte to said furnace atmosphere and a second surface to said reference medium;

detachably connecting an oxygen ion conducting compensation electrolyte means that comprises a solid body between a first contact electrode and a portion of said first surface for avoiding oxygen potential deviations of said measuring electrolyte at said first surface in said furnace atmosphere by eliminating contact between said first surface of said measuring electrolyte and said first contact electrode; and connecting a second contact electrode to a portion of said second surface in said reference medium.

15. A method according to claim 14, further comprising the step of detachably connecting a second solid body of said compensation electrolyte means between said second contact electrode and said portion of said second surface in said reference medium.

* * * * *